United States Patent
Woo et al.

(10) Patent No.: US 10,858,315 B2
(45) Date of Patent: Dec. 8, 2020

(54) METHOD FOR PREPARING (R)-N-[4-(1-AMINO-ETHYL)-2,6-DIFLUORO-PHENYL]-METHANESULFONAMIDE

(71) Applicant: AMOREPACIFIC CORPORATION, Seoul (KR)

(72) Inventors: Byoung Young Woo, Yongin-si (KR); Ki-Wha Lee, Yongin-si (KR); Jihae Lee, Yongin-si (KR); Chang Soon Choi, Yongin-si (KR); Miyoung Park, Yongin-si (KR); Young-Ho Park, Yongin-si (KR); Sarva Jayaprakash, Yongin-si (KR); Sridhar Regati, Yongin-si (KR); Mamidi Srinivas, Yongin-si (KR); Krushnakant Patel, Yongin-si (KR); M. Ramamohan, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/337,729

(22) PCT Filed: Sep. 26, 2017

(86) PCT No.: PCT/KR2017/010582
§ 371 (c)(1),
(2) Date: Mar. 28, 2019

(87) PCT Pub. No.: WO2018/062799
PCT Pub. Date: Apr. 5, 2018

(65) Prior Publication Data
US 2020/0031766 A1    Jan. 30, 2020

(30) Foreign Application Priority Data
Sep. 28, 2016 (KR) .................. 10-2016-0124642

(51) Int. Cl.
| C07C 311/08 | (2006.01) |
| B01D 9/00 | (2006.01) |
| C07C 303/44 | (2006.01) |
| B01L 9/00 | (2006.01) |

(52) U.S. Cl.
CPC .............. *C07C 311/08* (2013.01); *B01L 9/00* (2013.01); *C07C 303/44* (2013.01)

(58) Field of Classification Search
None
See application file for complete search history.

(56) References Cited

U.S. PATENT DOCUMENTS

| 2012/0008874 A1 | 4/2012 | Shishido et al. |
| 2017/0342027 A1 | 11/2017 | Woo et al. |

FOREIGN PATENT DOCUMENTS

| KR | 10-2000-0050905 A | 8/2000 |
| KR | 10-2009-0033916 A | 4/2009 |
| KR | 10-2016-0101554 A | 8/2016 |
| WO | 2007-129188 A1 | 11/2007 |
| WO | 2007-133637 A2 | 11/2007 |
| WO | 2008-013414 A1 | 1/2008 |
| WO | 2010/010934 A1 | 1/2010 |

OTHER PUBLICATIONS

Emese Palovics et al., Separation of the Mixtures of Chiral Compounds by Crystallization, Advances in Crystallization Processes, 2012, ISBN 978-953-51-0581-7, pp. 3-38.
Nguyen et al., International journal of Biomedical science, 2006, vol. 2, pp. 85-100.
Stinson et al., Chem. Eng. News, 1992, pp. 46-79.
International Search Report and Written Opinion for International Application No. PCT/KR2017/010582, dated Jan. 3, 2018.

*Primary Examiner* — Joseph R Kosack
(74) *Attorney, Agent, or Firm* — Merchant & Gould P.C.

(57) ABSTRACT

Disclosed in the present specification is a method capable of preparing N-[4-[(1R)-1-[[(R)-(1,1-dimethylethyl)sulfinyl]amino]ethyl]-2,6-difluorophenyl]-methanesulfonamide (INT028-2) with high optical purity, through the selection of Ellman-chiral auxiliaries and the recrystallization and separation of optical isomers. According to the above method, high-purity N-[4-[(1R)-1-[[(R)-(1,1-dimethylethyl)sulfinyl]amino]ethyl]-2,6-difluorophenyl]-methanesulfonamide with excellent quality can be produced at room temperature by improving cryogenic process conditions necessary for realizing high optical purity, and thus the trimming due to the process failure rate can be remarkably reduced.

16 Claims, 1 Drawing Sheet

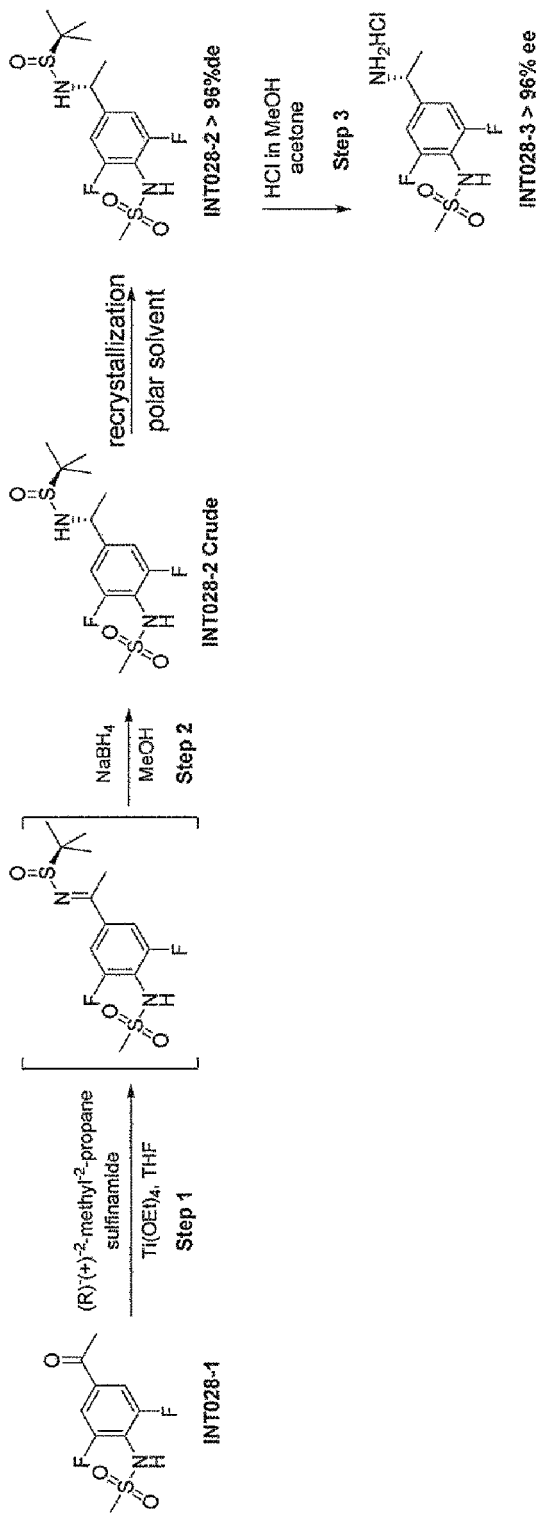

METHOD FOR PREPARING (R)-N-[4-(1-AMINO-ETHYL)-2,6-DIFLUORO-PHENYL]-METHANESULFONAMIDE

This application is a National Stage Application of International Application No. PCT/KR2017/010582, filed 26 Sep. 2017, which claims benefit of Serial No. 10-2016-0124642, filed 28 Sep. 2016 in the Republic of Korea and which applications are incorporated herein by reference. To the extent appropriate, a claim of priority is made to each of the above disclosed applications.

TECHNICAL FIELD

The present specification discloses a novel method for preparing an intermediate exhibiting chirality of (R)—N-[1-(3,5-difluoro-4-methanesulfonylamino-phenyl)-ethyl]-3-(2-propyl-6-trifluoromethyl-pyridin-3-yl)-acrylamide (PAC-14028).

BACKGROUND

Recently, the demand for sterically pure compounds has rapidly increased. One important use of such pure stereoisomers is their use as intermediates for synthesis in the pharmaceutical industry. For example, it has been increasingly revealed that enantiomerically pure drugs have more advantages than racemic drug mixtures. These advantages [literature example: Stinson, S. C., Chem. Eng. News, Sep. 28, 1992, pp. 46-79] often include decreased side effects and greater efficacy associated with enantiomerically pure compounds.

For example, triadimenol may have four isomers, and a (−)-(1S, 2R)-isomer exhibits higher activity than a (+)-(1R, 2R)-isomer and a (−)-(1S, 2S)-isomer exhibits higher activity than a (+)-(1R, 2S)-isomer. It is known that a (1R, 2R)-isomer among four isomers of dichlorobutrazole exhibits the highest activity. It is also known that (+)-(2S, 4S)- and (−)-(2S, 4R)-isomers of an etaconazole compound exhibit a higher sterilizing effect than the other isomers.

Hence, it is advantageous to selectively manufacture only one highly active isomer since a higher effect can be obtained by using a smaller amount and environmental pollution due to the use of chemicals can be decreased. Particularly, in the case of pharmaceuticals, it is significantly important to selectively manufacture only one isomer when another isomer is toxic to the human body.

Accordingly, in the fields of medicinal, pharmaceutical, and biochemical industries and the like, it is an extremely important task to manufacture an optically pure compound for the purpose of improving drug efficacy per unit and preventing the phytotoxicity by side effects.

However, a great number of medicines still have been used as racemic compounds which exhibit unavoidable side effects due to the presence of undesired enantiomers [literature example: Nguyen, et al., Chiral Drugs: An Overview, Int. J. Biomed. Sci., 2 (2006) 85-100]. Although some techniques may be used for chiral resolution on a preliminary or analytical scale, it takes a tremendous amount of time and effort to find the resolution technique according to the desired racemate. Even if resolution (separation) of the enantiomer is succeeded, there will be the next challenge, namely, the challenge of enabling chiral resolution on an industrial scale.

For example, the efficacy of pure stereoisomers of vanilloid antagonists including N-[4-(1-aminoethyl)-phenyl]-sulfonamide derivatives has been demonstrated [literature examples: WO 2008-013414 A1, WO 2007-133637 A2, WO 2007-129188 A1, and WO 2010-010934 A1].

An asymmetric synthesis method using the Ellman's auxiliary is known as a synthesis method for preparing a single isomer of such a N-[4-(1-aminoethyl)-phenyl]-sulfonamide derivative. For example, WO 2008-013414 A1, WO 2007-133637 A2, WO 2007-129188 A1, and WO 2010-010934 A1 propose a method for obtaining the desired stereoisomer by introduction of Ellman's auxiliary and induction of asymmetric reduction using this. However, this method is a method capable of selectively obtaining an optical isomer only depending on the specificity of the chiral auxiliary, and there is thus a limit to obtain a high optical purity. In addition, it takes a great amount of time and effort since the method requires complicated process conditions that it is required to maintain the temperature for reaction at a low temperature of about −50° C. in order to increase the optical purity (enantiomeric excess, ee %), the process failure rate is high since the method is sensitive to the reaction temperature and the optical purity is lowered by temperature control, and the quality of new drug developed may be adversely affected.

SUMMARY OF INVENTION

Technical Problem

Accordingly, an object of the present invention is to provide a novel method which can manufacture (R)—N-[4-(1-amino-ethyl)-2,6-difluoro-phenyl]-methanesulfonamide (INT028-3) which is an intermediate of the new drug substance and has a significantly high optical purity of an optical isomer by using the Ellman's chiral auxiliary.

Solution to Problem

In order to achieve the above object, an aspect of the present invention provides a method for preparing (R)—N-[4-(1-amino-ethyl)-2,6-difluoro-phenyl]-methanesulfonamide, which includes a recrystallization step including putting and stirring a stereoisomeric mixture in which optical isomers of N-[4-[(1R)-1-[[(R)-(1,1-dimethylethyl)sulfinyl]amino]ethyl]-2,6-difluorophenyl]-methanesulfonamide are mixed in a specific solvent and obtaining a solid which is precipitated in the solution phase and contains N-[4-[(1R)-1-[[(R)-(1,1-dimethylethyl)sulfinyl]amino]ethyl]-2,6-difluorophenyl]-methanesulfonamide.

Advantageous Effects of Invention

The method according to an aspect of the present invention can manufacture N-[4-(1-amino-ethyl)-2,6-difluoro-phenyl]-methanesulfonamide (INT028-3) which is an intermediate of (R)—N-[1-(3,5-difluoro-4-methanesulfonylamino-phenyl)-ethyl]-3-(2-propyl-6-trifluoromethyl-pyridin-3-yl)-acrylamide (PAC-14028) of a new drug substance, exhibits chirality, and has a high optical purity through the recrystallization separation of optical isomers while utilizing the selectivity of the Ellman's chiral auxiliary. In the method according to an aspect of the present invention, N-[4-(1-amino-ethyl)-2,6-difluoro-phenyl]-methanesulfonamide (INT028-3) having a high optical purity can be obtained by using recrystallization separation as a subsequent step in order to overcome the limitation of the Ellman's chiral auxiliary having a low optical purity at room temperature. This makes it possible to avoid the severe cryogenic conditions in the Ellman's auxiliary process for achieving a high optical purity. In other words, it is possible to avoid the low-temperature process and to remarkably decrease the loss due to the process failure rate in the manufacture of medicines from new drug raw materials by implementing a method for increasing the optical purity of the Ellman's auxiliary having a low optical purity at room temperature by recrystallization separation.

BRIEF DESCRIPTION OF DRAWINGS

FIG. 1 is a diagram illustrating a mechanism for manufacturing (R)—N-[4-(l-amino-ethyl)-2,6-difluoro-phenyl]-methanesulfonamide (INT028-3) from N-(4-acetyl-2,6-difluorophenyl)-methanesulfonamide (INT028-1).

DESCRIPTION OF EMBODIMENTS

Hereinafter, embodiments of the present invention will be described in detail with reference to FIG. 1.

The optical purity of (R)—N-[4-(l-amino-ethyl)-2,6-difluoro-phenyl]-methanesulfonamide (INT028-3) of an intermediate is significantly important in order to manufacture (R)—N-[1-(3,5-difluoro-4-methanesulfonylamino-phenyl)-ethyl]-3-(2-propyl-6-trifluoromethyl-pyridin-3-yl)-acrylamide (PAC-14028) of a new drug substance. The method for preparing (R)—N-[4-(1-amino-ethyl)-2,6-difluoro-phenyl]-methanesulfonamide (INT028-3) of the intermediate having a high optical purity is a significantly important factor in the quality control of drugs.

In the method for synthesizing (R)—N-[4-(l-amino-ethyl)-2,6-difluoro-phenyl]-methanesulfonamide (INT028-3) of the intermediate from N-(4-acetyl-2,6-difluorophenyl)-methanesulfonamide (INT028-1) by utilizing the Ellman's chiral auxiliary, the optical purity of N-[4-[(1R)-1-[[(R)-(1,1-dimethylethyl)sulfinyl]amino]ethyl]-2,6-difluorophenyl]-methanesulfonamide (INT028-2) determines the optical purity of (R)—N-[4-(l-amino-ethyl)-2,6-difluoro-phenyl]-methanesulfonamide (INT028-3). Specifically, the optical purity is determined in the reduction reaction in Step 2 of FIG. 1, and (R)—N-[4-(1-amino-ethyl)-2,6-difluoro-phenyl]-methanesulfonamide (INT028-3) is manufactured by removing the Ellman's chiral auxiliary from N-[4-[((R)-1-[[(R)-(1,1-dimethylethyl)sulfinyl]amino]ethyl]-2,6-difluorophenyl]-methanesulfonamide (INT028-2) through Step 3.

In the present specification, N-(4-acetyl-2,6-difluorophenyl)-methanesulfonamide is a compound with the CAS No. 956901-21-6, which means that the molecular weight thereof corresponds to 249.23 Da, and it can be used interchangeably with INT028-1 in the present specification.

In the present specification, N-[4-[(1R)-1-[[(R)-(1,1-dimethylethyl)sulfinyl]amino]ethyl]-2,6-difluorophenyl]-methanesulfonamide is a compound with the CAS No. 956901-22-7, which means that the molecular weight thereof corresponds to 354.44 Da, and it can be used interchangeably with INT028-2 in the present specification.

In the present specification, (R)—N-[4-(l-amino-ethyl)-2,6-difluoro-phenyl]-methanesulfonamide means a substance corresponding to the CAS No. 956901-23-8, and it can be used interchangeably with the R-isomer of INT028-3 in the present specification.

In the present specification, (R)—N-[1-(3,5-difluoro-4-methanesulfonylamino-phenyl)-ethyl]-3-(2-propyl-6-trifluoromethyl-pyridin-3-yl)-acrylamide (PAC-14028) corresponds to the CAS No. 1005168-10-4, which means that the molecular weight thereof corresponds to 491.47 Da.

In the present specification, the Ellman's chiral auxiliary means an effective chiral auxiliary for manufacturing a chiral amine compound.

In the conventional method using the Ellman's chiral auxiliary, there is a problem that the optical purity is remarkably low when the temperature for reaction is higher than −5° C. in Step 2. Hence, there are difficulties in the process since it is required to control the temperature for reaction to a low temperature of −48° C. in order to manufacture (R)—N-[4-(1-amino-ethyl)-2,6-difluoro-phenyl]-methanesulfonamide (INT028-3), and the process failure rate due to temperature control is high since the reaction is sensitive to temperature.

Accordingly, the present invention is intended to provide a method for preparing (R)—N-[4-(l-amino-ethyl)-2,6-difluoro-phenyl]-methanesulfonamide (INT028-3) having a high optical purity even by a reaction using the Ellman's chiral auxiliary at room temperature.

An embodiment of the present invention is a method for preparing (R)—N-[4-(l-amino-ethyl)-2,6-difluoro-phenyl]-methanesulfonamide (INT028-3), which may include a recrystallization step including putting and stirring a stereoisomeric mixture in which optical isomers of N-[4-[(1R)-1-[[(R)-(1,1-dimethylethyl)sulfinyl]amino]ethyl]-2,6-difluorophenyl]-methanesulfonamide having a low optical purity are mixed in a solvent and obtaining a solid which is precipitated in the solution phase and contains N-[4-[(1R)-1-[[(R)-(1,1-dimethylethyl)sulfinyl]amino]ethyl]-2,6-difluorophenyl]-methanesulfonamide.

The solvent in the recrystallization step according to an embodiment may include one or more kinds selected from the group consisting of isopropyl alcohol (IPA), methanol (MeOH), ethyl acetate (EtOAc), toluene, and isopropyl acetate.

More specifically, in an embodiment, the solvent in the recrystallization step may include those selected from the group consisting of isopropyl alcohol (IPA), methanol:ethyl acetate (MeOH:EtOAc) (1:8), methanol:ethyl acetate (1:6), ethyl acetate (EtOAc), ethyl acetate:toluene (1:2), ethyl acetate:toluene (1:1), and isopropyl acetate. In the recrystallization step, (R)—N-[4-[(1R)-1-[[(R)-(1,1-dimethylethyl)sulfinyl]amino]ethyl]-2,6-difluorophenyl]-methanesulfonamide (INT028-2) having a high optical purity can be obtained from a stereoisomeric mixture in which optical isomers of N-[4-[(1R)-1-[[(R)-(1,1-dimethylethyl)sulfinyl]amino]ethyl]-2,6-difluorophenyl]-methanesulfonamide are mixed as N-[4-[(1R)-1-[[(R)-(1,1-dimethylethyl)sulfinyl]amino]ethyl]-2,6-difluorophenyl]-methanesulfonamide specifically reacts with the solvent. More specifically, the solvent may be isopropyl alcohol (IPA).

In an embodiment, the temperature for stirring in the recrystallization step may be −5° C. to 35° C., but it is not limited thereto. Specifically, the temperature for stirring may be −5° C. or higher, 0° C. or higher, 5° C. or higher, 10° C. or higher, 15° C. or higher, 20° C. or higher, 25° C. or higher, 30° C. or higher, or 35° C. or higher and 50° C. or lower, 45° C. or lower, 40° C. or lower, 35° C. or lower, 30° C. or lower, 25° C. or lower, 20° C. or lower, 15° C. or lower, 10° C. or lower, or 5° C. or lower, 0° C. or lower, or −5° C. or lower. More specifically, the temperature for stirring may be from −5° C. to 5° C., from −5° C. to 10° C., from 10° C. to 20° C., or from 20° C. to 35° C., but it is not limited thereto.

As an embodiment, the recrystallization step may further include filtering the precipitated solid to obtain N-[4-[(1R)-1-[[(R)-(1,1-dimethylethyl)sulfinyl]amino]ethyl]-2,6-difluorophenyl]-methanesulfonamide (INT028-2).

In an embodiment of the present invention, the time for stirring may be 1 hour or longer, 3 hours or longer, 5 hours or longer, 8 hours or longer, 10 hours or longer, 11 hours or longer, 12 hours or longer, 13 hours or longer, 14 hours or longer, 15 hours or longer, 16 hours or longer, 17 hours or longer, 18 hours or longer, 19 hours or longer, 20 hours or longer, 30 hours or longer, 40 hours or longer, 50 hours or longer, or 100 hours or longer or 100 hours or shorter, 80 hours or shorter, 50 hours or shorter, 40 hours or shorter, 30 hours or shorter, 20 hours or shorter, 19 hours or shorter, 18 hours or shorter, 17 hours or shorter, 16 hours or shorter, 15 hours or shorter, 14 hours or shorter, 13 hours or shorter, 12 hours or shorter, 11 hours or shorter, 10 hours or shorter, 8 hours or shorter, 5 hours or shorter, 4 hours or shorter, 3 hours or shorter, or 1 hour or shorter. Specifically, the time for stirring may be 5 hours or longer and 50 hours or shorter, and more particularly, the time for stirring may be from 10 hours to 15 hours.

In an embodiment of the present invention, the stereoisomeric mixture in which optical isomers of N-[4-[(1R)-1-[[(R)-(1,1-dimethylethyl)sulfinyl]amino]ethyl]-2,6-difluorophenyl]-methanesulfonamide are mixed is an optically active isomeric compound, and it may mean a mixture of two diastereoisomers, and the mixing ratio at this time may be R,R optical isomer:optical isomers other than R,R optical isomer=1:1 (corresponding to a racemic mixture) or the mixing ratio may correspond to a ratio of integers between R,R optical isomer:optical isomers other than R,R optical isomer=1:1 to 97:3. In an embodiment of the present invention, the stereoisomeric mixture may be an artificially synthesized mixture or a mixture in which the ratio of the R optical isomer to the S optical isomer is not known. According to the method of the present invention, it is possible to remarkably increase the ratio of either one of the R optical isomer or the S optical isomer and thus to obtain the optical isomer having a desired form and a high optical purity irrespective of the ratio in the mixture. As a more specific embodiment, an optical purity of about 90% can be obtained when the mixing ratio is 1:10 and an optical purity of about 94% can be obtained when the mixing ratio is 97:3.

In addition, according to an embodiment of the present invention, the method may further include adding R-2-methyl-propanesulfinamide and titanium (ethoxide)$_4$ (Ti(OEt)$_4$) to a solution containing N-(4-acetyl-2,6-difluorophenyl)-methanesulfonamide and mixing these together and then adding borohydride to the mixture and reacting the mixture with the borohydride to synthesize N-[4-[(1R)-1-[[(R)-(1,1-dimethylethyl) sulfinyl]amino]ethyl]-2,6-difluorophenyl]-methanesulfonamide as a step of synthesizing the stereoisomeric mixture prior to the recrystallization step.

As an embodiment, the borohydride may include every borohydride without limitation as long as it can be subjected to the borohydride reduction, and specific examples thereof may include sodium borohydride (NaBH$_4$), sodium cyanoborohydride (NaBH$_3$CN), or triacetoxyborohydride (NaHB(OAc)$_3$). The temperature for the reaction with borohydride may be from −50° C. to 35° C. and specifically from −5° C. to 35° C. In other words, the present invention includes the recrystallization step, it is thus not required to maintain the temperature in Step 2 at a low temperature of −48° C. as in the conventional method, and Step 2 may be performed at −5° C. or higher. Specifically, the reaction with borohydride may be conducted with stirring, and the temperature for stirring may be −5° C. or higher, 0° C. or higher, 5° C. or higher, 10° C. or higher, 15° C. or higher, 20° C. or higher, 25° C. or higher, 30° C. or higher, or 35° C. or higher, and the temperature for stirring may be 50° C. or lower, 45° C. or lower, 40° C. or lower, 35° C. or lower, 30° C. or lower, 25° C. or lower, 20° C. or lower, 15° C. or lower, 10° C. or lower, 5° C. or lower, 0° C. or lower, or −5° C. or lower. More specifically, the temperature for stirring may be from −5° C. to 5° C., from −5° C. to 10° C., from 10° C. to 20° C., or from 20° C. to 35° C., but it is not limited thereto.

In an embodiment of the present invention, the time for stirring may be 1 hour or longer, 3 hours or longer, 5 hours or longer, 8 hours or longer, 10 hours or longer, 11 hours or longer, 12 hours or longer, 13 hours or longer, 14 hours or longer, 15 hours or longer, 16 hours or longer, 17 hours or longer, 18 hours or longer, 19 hours or longer, 20 hours or longer, 30 hours or longer, 40 hours or longer, 50 hours or longer, or 100 hours or longer or 100 hours or shorter, 80 hours or shorter, 50 hours or shorter, 40 hours or shorter, 30 hours or shorter, 20 hours or shorter, 19 hours or shorter, 18 hours or shorter, 17 hours or shorter, 16 hours or shorter, 15 hours or shorter, 14 hours or shorter, 13 hours or shorter, 12 hours or shorter, 11 hours or shorter, 10 hours or shorter, 8 hours or shorter, 5 hours or shorter, 4 hours or shorter, 3 hours or shorter, or 1 hour or shorter. Specifically, the time for stirring may be 5 hours or longer and 50 hours or shorter and more specifically, the time for stirring may be from 10 hours to 15 hours.

As an embodiment, the solution containing N-(4-acetyl-2,6-difluorophenyl)-methanesulfonamide (INT028-1) may be prepared by dissolving N-(4-acetyl-2,6-difluorophenyl)-methanesulfonamide in an aprotic solvent. The aprotic solvent is not limited as long as it can dissolve N-(4-acetyl-2,6-difluorophenyl)-methanesulfonamide, and examples thereof may include tetrahydrofuran (THF), dichloromethane (CH$_2$Cl$_2$), diethyl ether (Et$_2$O), and toluene.

As an embodiment, the equivalent ratio of R-2-methyl-propanesulfinamide to titanium (ethoxide)$_4$ (Ti(OEt)$_4$) added to the solution prepared by dissolving N-(4-acetyl-2,6-difluorophenyl)-methanesulfonamide in an aprotic solvent may be from 1:1 to 1:0.5.

As an embodiment, the step of synthesizing the stereoisomeric mixture may further include cooling the mixture after the synthesis reaction of the mixture. As an embodiment, in the step of synthesizing the stereoisomeric mixture, filtration, neutralization, and extraction may be conducted in order to purify the mixture, and the step may further include concentrating the mixture under reduced pressure and purifying the mixture.

In addition, the method according to an embodiment of the present invention may further include a step of obtaining (R)—N-[4-(l-amino-ethyl)-2,6-difluoro-phenyl]-methanesulfonamide by mixing the solid containing N-[4-[(1R)-1-[[(R)-(1,1-dimethylethyl)sulfinyl]amino]ethyl]-2,6-difluorophenyl]-methanesulfonamide with a hydrochloric acid (HCl) solution after the recrystallization step. More specifically, the step may be to mix the solid with methanol and a hydrochloric acid solution having a normality of from 3N to 6N. As an embodiment, the step may further include mixing the solid with a hydrochloric acid solution having a normality of from 3N to 6N, then concentrating the mixture under reduced pressure, and purifying the mixture with acetone to obtain (R)—N-[4-(l-amino-ethyl)-2,6-difluoro-phenyl]-methanesulfonamide.

According to the method of an embodiment of the present invention described above, it is possible to provide an R optical isomer of N-[4-(l-amino-ethyl)-2,6-difluoro-phenyl]-methanesulfonamide, namely, (R)—N-[4-(l-amino-ethyl)-2,6-difluoro-phenyl]-methanesulfonamide having a high optical purity. In the present specification, the term "high optical purity" is a term well known in the art of the present invention, and as an embodiment, the term "high optical purity" may be to have an optical purity value (enantiomeric excess, ee %) of 80% or more, 90% or more, 95% or more, 96% or more, 97% or more, 98% or more, or 99% or more. Specifically, the optical purity of (R)—N-[4-(1-amino-ethyl)-2,6-difluoro-phenyl]-methanesulfonamide manufactured according to an embodiment of the present invention may be 96% or more and less than 100%.

The R isomer resolved by the method according to an embodiment of the present invention can be used as an intermediate in the manufacture of the novel drug described in Korean Patent Application No. 10-2009-700433 by being reacted with the substance described in the application. Accordingly, the present invention may relate to a method for preparing the novel drug described in Korean Patent Application No. 10-2009-700433 by using the R stereoisomer resolved by the method according to an embodiment of the present invention or a novel drug manufactured by such a method in an embodiment.

The present invention may relate to (R)—N-[1-(3,5-difluoro-4-methanesulfonylamino-phenyl)-ethyl]-3-(2-propyl-6-trifluoromethyl-pyridin-3-yl)-acrylamide having an enantiomeric excess of 96% or more, 97% or more, 98%, or more, 99% or more, or from 96% and 99% manufactured by the method according to an embodiment of the present invention in an embodiment.

An embodiment of the present invention can provide a TRPV1 antagonist containing (R)—N-[1-(3,5-difluoro-4-methanesulfonylamino-phenyl)-ethyl]-3-(2-propyl-6-trifluoromethyl-pyridin-3-yl)-acrylamide (PAC-14028) manufactured by the method according to an embodiment of the present invention as an active ingredient. Such a TRPV1 antagonist can be used in pharmaceutical compositions for the prevention or treatment of the diseases to be described below.

Furthermore, the present invention may relate to a pharmaceutical composition for the prevention or treatment of diseases associated with pathological stimulation and/or abnormal expression of a vanilloid receptor selected from the group consisting of pain, inflammatory disease of the joint, neurological disorder, HIV-related neurological disorder, nerve damage, neurodegeneration, stroke, urinary incontinence, cystitis, stomach-duodenal ulcer, irritable bowel syndrome (IBS) and inflammatory bowel disease (IBD), bowel ulceration, gastroesophageal reflux disease (GERD), Crohn's disease, asthma, chronic obstructive pulmonary disease, cough, neurogenic/allergic/inflammatory skin disease, psoriasis, ovulation, skin irritation, eye or mucous membrane inflammation, auditory hypersensitivity, tinnitus, vestibular hypersensitivity, episodic vertigo, myocardial ischemia, hairy hair, hair loss, alopecia, rhinitis, and pancreatitis containing (R)—N-[1-(3,5-difluoro-4-methanesulfonylamino-phenyl)-ethyl]-3-(2-propyl-6-trifluoromethyl-pyridin-3-yl)-acrylamide according to an embodiment of the present invention, an optical isomer thereof, or a pharmaceutically acceptable salt thereof and a pharmaceutically acceptable carrier in one embodiment.

In an embodiment of the present invention disclosed in the present specification, the pain may be a disease selected from the group consisting of osteoarthritis, rheumatoid arthritis, ankylosing spondylitis, diabetic neuropathic pain, post-operative pain, toothache, fibromatosis, myofascial pain syndrome, back pain, migraine, and other types of headache or pain associated with the disease.

EMBODIMENTS

Hereinafter, the present invention will be described with reference to the following Examples and Test Examples. Examples and Test Examples are provided for illustrating the present invention in more detail, and the scope of the present invention is not limited to the range of the following Examples.

Comparative Test Example 1

A conventional asymmetric synthesis method was performed as follows to synthesize a stereoisomeric mixture of N-[4-[(1R)-1-[[(R)-(1,1-dimethylethyl)sulfinyl]amino]ethyl]-2,6-difluorophenyl]-methanesulfonamide (INT028-2).

Specifically, 30 g (1 equivalent) of N-(4-acetyl-2,6-difluorophenyl)-methanesulfonamide (INT028-1) was added to and dissolved in 300 ml of tetrahydrofuran (THF), and R-2-methyl-propanesulfinamide and titanium (ethoxide)$_4$ (Ti(OEt)$_4$) were then added to the solution in an amount to be 1.3 equivalents to 1 equivalent of N-(4-acetyl-2,6-difluorophenyl)-methanesulfonamide (INT028-1) and 2 equivalents to 1 equivalent of N-(4-acetyl-2,6-difluorophenyl)-methanesulfonamide (INT028-1), respectively. The mixture was then stirred for 16 hours while being refluxed.

The stirred solution was cooled to a temperature of Comparative Example 1 (−48° C.), Comparative Example 2 (−5° C. to +5° C.), and Comparative Example 3 (20° C. to 25° C.), NaBH$_4$ was then added to the solution in an amount to be 4 equivalents to 1 equivalent of the stereoisomeric mixture, and the mixture was stirred again for 12 hours. Saturated NaCl (aq) was added to the resultant mixture, the resultant solid was filtered off, and the filtrate was neutralized, extracted with ethyl acetate, and concentrated.

TABLE 1

| | Temperature for stirring and reaction (° C.) | INT028-2 (de %) |
|---|---|---|
| Comparative Example 1 | −48 | 96.4 |
| Comparative Example 2 | −5~+5 | 74.1 |
| Comparative Example 3 | 20~25 | 72.2 |

As a result, it has been confirmed that it is required to control the temperature for reaction to a low temperature as in Comparative Example 1 in order to manufacture INT028-2 having a high optical purity in the prior art and the optical purity (diastereomeric excess, de) is remarkably low when the temperature for reaction is −5° C. or higher as presented in Table 1.

Test Example 1

According to an embodiment of the present invention, (R)—N-[4-(1-amino-ethyl)-2,6-difluoro-phenyl]-methanesulfonamide (INT028-3) was manufactured.

First, the solvents presented in the following Table 2 were respectively added to the solid of Comparative Example 2 (INT028-2) manufactured by the method in Comparative Experiment Example 1, and a recrystallization step to filter the solid to be precipitated in the solution phase by stirring at various temperatures was then performed.

TABLE 2

| | Temperature for stirring (° C.) | Solvent | INT028-2 (de %) |
|---|---|---|---|
| Comparative Example 2 | 20~35 | — | 74.1 |
| Example 1 | | IPA | 99.1 |
| Example 2 | | MeOH:EtOAc = 1/8 | 98.4 |
| Example 3 | | MeOH:EtOAc = 1/6 | 98.7 |
| Example 4 | | EtOAc | 96.3 |
| Example 5 | | EtOAc:Toluene = 1:2 | 96.1 |
| Example 6 | | EtOAc:Toluene = 1:1 | 96.7 |
| Example 7 | | Isopropyl acetate | 96.6 |
| Comparative Example 4 | | Methanol | — |
| Comparative Example 5 | | Ethanol | — |
| Comparative Example 6 | | Toluene | 76.4 |
| Example 8 | −5~+10 | IPA | 96.4 |
| Example 9 | | MeOH:EtOAc = 1/8 | 96.1 |
| Example 10 | | Isopropyl acetate | 94.1 |
| Example 11 | +10~+20 | IPA | 97.6 |
| Example 12 | | MeOH:EtOAc = 1/8 | 97.2 |
| Example 13 | | Isopropyl acetate | 96.0 |

As a result, it has been confirmed that the optical purity in Examples 1 to 7 in which the recrystallization step has been conducted at the same temperature for stirring in order to compare the results of optical purity of INT028-2 of Comparative Example 2 having a low optical purity depending on the solvent sharply has increased to 96de % or more as presented in [Table 2]. From Examples 1 to 7, Examples 8 to 10, and Examples 11 to 13 above, it can be seen that the recrystallization step is not affected by the temperature for stirring and a high optical purity of 96% or more is obtained even at room temperature in all Examples. According to the present invention, the low-temperature process can be avoided and the process scale can be thus more easily increased.

In addition, INT028-2 was reacted only with a specific solvent in the recrystallization step so that INT028-2 was completely dissolved in the solvent when methanol or ethanol was used as a solvent as in Comparative Examples 4 to 6 and the optical purity was low when toluene was used as a solvent. Among the various solvents, the optical purity was the most favorable in the case of the IPA solvent in Example 1, and it is thus judged that the IPA solvent can be most efficiently applied in the process since it is a single solvent.

The above results mean that INT028-3 having an optical purity of 96% or more can be obtained by remarkably increasing the optical purity through the recrystallization step even in the case of a mixture having a low optical purity at room temperature since INT028-2 has been synthesized according to the conventional method.

The results obtained by repeatedly performing the process in Example 1 three times are presented in the following Table 3, and the results mean that INT028-3 having a high optical purity can be manufactured by a stable process since the method according to an embodiment of the present invention exhibits reproducibility.

TABLE 3

| Example | Amount of INT028-1 put | INT028-2 (de %) | INT028-3 (ee %) |
|---|---|---|---|
| 1 | 30 g | 99.7 | 99.9 |
| 1 | 30 g | 99.7 | 99.9 |
| 1 | 30 g | 99.7 | 99.9 |

The invention claimed is:

1. A method for preparing a salt of (R)—N-[4-(1-aminoethyl)-2,6-difluoro-phenyl]-methanesulfonamide, the method comprising:
   a recrystallization step including putting and stirring a stereoisomeric mixture in which optical isomers of N-[4-[(1R)-1-[[(R)-(1,1-dimethylethyl)sulfinyl]amino]ethyl]-2,6-difluorophenyl]-methanesulfonamide are mixed in a specific solvent and obtaining a solid which is precipitated in a solution phase and contains N-[4-[(1R)-1-[[(R)-(1,1-dimethylethyl)sulfinyl]amino]ethyl]-2,6-difluorophenyl]-methanesulfonamide,
   wherein
   the solvent in the recrystallization step includes one or more kinds selected from the group consisting of isopropyl alcohol (IPA), methanol (MeOH), ethyl acetate (EtOAc), toluene, and isopropyl acetate,
   wherein the method further comprises a step of converting the solid to a salt of (R)—N-[4-(1-aminoethyl)-2,6-difluoro-phenyl]-methanesulfonamide after the recrystallization step.

2. The method for preparing a salt of (R)—N-[4-(1-aminoethyl)-2,6-difluoro-phenyl]-methanesulfonamide according to claim 1, wherein the solvent in the recrystallization step is selected from the group consisting of isopropyl alcohol (IPA), methanol:ethyl acetate (MeOH:EtOAc) (1:8), methanol:ethyl acetate (1:6), ethyl acetate (EtOAc), ethyl acetate:toluene (1:2), ethyl acetate:toluene (1:1), and isopropyl acetate.

3. The method for preparing a salt of (R)—N-[4-(1-aminoethyl)-2,6-difluoro-phenyl]-methanesulfonamide according to claim 1, wherein the solvent in the recrystallization step is isopropyl alcohol (IPA).

4. The method for preparing a salt of (R)—N-[4-(1-aminoethyl)-2,6-difluoro-phenyl]-methanesulfonamide according to claim 1, wherein a temperature for stirring in the recrystallization step is from −5° C. to 35° C.

5. The method for preparing a salt of (R)—N-[4-(1-aminoethyl)-2,6-difluoro-phenyl]-methanesulfonamide according to claim 1, wherein a temperature for stirring in the recrystallization step is from 20° C. to 35° C.

6. The method for preparing a salt of (R)—N-[4-(1-aminoethyl)-2,6-difluoro-phenyl]-methanesulfonamide according to claim 1, wherein a temperature for stirring in the recrystallization step is from −5° C. to 5° C.

7. The method for preparing a salt of (R)—N-[4-(1-aminoethyl)-2,6-difluoro-phenyl]-methanesulfonamide according to claim 1, wherein the recrystallization step further includes filtering the precipitated solid.

8. The method for preparing a salt of (R)—N-[4-(1-aminoethyl)-2,6-difluoro-phenyl]-methanesulfonamide according to claim 1, further comprising:
   adding R-2-methyl-propanesulfinamide and titanium (ethoxide)4 (Ti(OEt)4) to a solution containing N-(4-acetyl-2,6-difluorophenyl)-methanesulfonamide and mixing these together and then
   adding borohydride to the mixture and reacting the mixture with the borohydride to synthesize N-[4-[(1R)-1-[

[(R)-(1,1-dimethylethyl)sulfinyl]amino]ethyl]-2,6-difluorophenyl]-methanesulfonamide,
as a step of synthesizing the stereoisomeric mixture prior to the recrystallization step.

9. The method for preparing a salt of (R)—N-[4-(1-aminoethyl)-2,6-difluoro-phenyl]-methanesulfonamide according to claim 8, wherein a temperature for the reaction with borohydride is from −5° C. to 35° C.

10. The method for preparing a salt of (R)—N-[4-(1-aminoethyl)-2,6-difluoro-phenyl]-methanesulfonamide according to claim 8, wherein the solution containing N-(4-acetyl-2,6-difluorophenyl)-methanesulfonamide is prepared by dissolving N-(4-acetyl-2,6-difluorophenyl)-methanesulfonamide in an aprotic solvent.

11. The method for preparing a salt of (R)—N-[4-(1-aminoethyl)-2,6-difluoro-phenyl]-methanesulfonamide according to claim 10, wherein an equivalent ratio of R-2-methyl-propanesulfinamide to titanium (ethoxide)4 (Ti(OEt)4) added to the solution prepared by dissolving N-(4-acetyl-2,6-difluorophenyl)-methanesulfonamide in an aprotic solvent is from 1:1 to 1:0.5.

12. The method for preparing a salt of (R)—N-[4-(1-aminoethyl)-2,6-difluoro-phenyl]-methanesulfonamide according to claim 8, wherein the step of synthesizing a stereoisomeric mixture further includes concentrating the mixture under reduced pressure and then purifying the mixture.

13. The method for preparing a salt of (R)—N-[4-(1-aminoethyl)-2,6-difluoro-phenyl]-methanesulfonamide according to claim 1, comprising:

a step of obtaining a salt of (R)—N-[4-(1-amino-ethyl)-2,6-difluoro-phenyl]-methanesulfonamide by mixing the solid containing N-[4-[(1R)-1-[[(R)-(1,1-dimethylethyl)sulfinyl]amino]ethyl]-2,6-difluorophenyl]-methanesulfonamide with an acid solution after the recrystallization step.

14. The method for preparing a salt of (R)—N-[4-(1-aminoethyl)-2,6-difluoro-phenyl]-methanesulfonamide according to claim 13, wherein the salt of (R)—N-[4-(1-amino-ethyl)-2,6-difluoro-phenyl]-methanesulfonamide is (R)—N-[4-(1-amino-ethyl)-2,6-difluoro-phenyl]-methanesulfonamide.HCl and the acid solution is a hydrochloric acid (HCl) solution.

15. The method for preparing a salt of (R)—N-[4-(1-aminoethyl)-2,6-difluoro-phenyl]-methanesulfonamide according to claim 14, wherein the step of obtaining a salt of (R)—N-[4-(1-amino-ethyl)-2,6-difluoro-phenyl]-methanesulfonamide includes mixing the solid with a hydrochloric acid solution having a normality of from 3N to 6N, then concentrating the mixture under reduced pressure, and purifying the mixture with acetone to obtain (R)—N-[4-(1-amino-ethyl)-2,6-difluoro-phenyl]-methanesulfonamide.HCl.

16. The method for preparing a salt of (R)—N-[4-(1-aminoethyl)-2,6-difluoro-phenyl]-methanesulfonamide according to claim 1, wherein an optical purity of a salt of (R)—N-[4-(1-amino-ethyl)-2,6-difluoro-phenyl]-methanesulfonamide manufactured by the method is 96% or more and less than 100%.

* * * * *